(12) United States Patent
Martínez et al.

(10) Patent No.: US 7,570,042 B2
(45) Date of Patent: Aug. 4, 2009

(54) METHOD FOR EVALUATING THE EFFECT OF AN ELECTRIC DISCHARGE ON A COMPOSITE MATERIAL

(75) Inventors: Valentín García Martínez, Madrid (ES); José Ignacio López-Reina Torrijos, Madrid (ES); Raúl Fernández Recio, Madrid (ES)

(73) Assignee: Airbus Espana, S.L., Madrid (ES)

( * ) Notice: Subject to any disclaimer, the term of this patent is extended or adjusted under 35 U.S.C. 154(b) by 301 days.

(21) Appl. No.: 11/807,902

(22) Filed: May 30, 2007

(65) Prior Publication Data

US 2008/0258705 A1 Oct. 23, 2008

(30) Foreign Application Priority Data

Mar. 30, 2007 (ES) ................. 200700858

(51) Int. Cl.
*G01N 27/00* (2006.01)
*G01N 25/00* (2006.01)
*G01R 29/12* (2006.01)
(52) U.S. Cl. ............................ 324/71.1; 324/457; 374/8
(58) Field of Classification Search ................ 324/71.1, 324/457; 374/5, 8, 45, 57
See application file for complete search history.

(56) References Cited

U.S. PATENT DOCUMENTS 2,386,647 A * 10/1945 Andresen ................ 361/218
4,323,946 A * 4/1982 Traux .................... 361/218
4,531,691 A * 7/1985 Boulay et al. ............. 244/1 A
6,900,642 B2 * 5/2005 Zank et al. ............... 324/457

* cited by examiner

*Primary Examiner*—Timothy J Dole
*Assistant Examiner*—Farhana Hoque
(74) *Attorney, Agent, or Firm*—Ladas and Parry LLP

(57) ABSTRACT

The present invention relates to a method for evaluating the effect of an electric discharge on an aircraft structure through the evaluation of the damage caused by the effect of the thermal heating generated by the mentioned discharge on the structure, including the steps of: applying an electric discharge on the material of the aircraft structure using an intensity generator; distributing in an electric mesh with resistive electric elements the material of the aircraft structure; calculating the intensities running through the electric mesh of the material of the aircraft structure from the intensity introduced in the generators; calculating with the previous intensities the heat which is dissipated in each of the elements of the electric mesh of the material of the aircraft structure; calculating the distribution of temperatures in each of the elements of the electric mesh of the material of the aircraft structure; determining the elements of the electric mesh of the material of the aircraft structure which, due to the effect of the distribution of temperatures, experience a change of state and evaporate; and determining the damage caused to the material of the aircraft structure due to the effect of the electric discharge

10 Claims, 2 Drawing Sheets

METHOD FOR EVALUATING THE EFFECT OF AN ELECTRIC DISCHARGE ON A COMPOSITE MATERIAL

FIELD OF THE INVENTION

The present invention relates to a method for evaluating the effect of an electric discharge on a composite material through the damage caused due to the effect of thermal heating.

BACKGROUND OF THE INVENTION

The evaluation of the thermal behavior of a material due to a severe electric discharge is required in the event that this material is in contact with areas in which there is a possible risk of ignition, for example and for the aeronautical field, in areas in contact with the fuel of the aircraft and/or with its gases. In this case, a prediction of the temperature reached in the material is required for the purpose of being able to prevent hot spots: the high current density in certain spot locations of the structure of the aircraft may cause high temperature spots. If this temperature exceeds 200° C. (ignition point of fuel considered by the FAA/JAA), the fuel may reach its inflammation point if the suitable concentrations are present inside the tank.

Structural damage (holes, melted material, peeling in the case of composite materials, etc.), which need to be known in order to prevent the mechanical behavior of the material after the impact, may occur due to thermal effects.

Until now aircraft structures have been manufactured mainly using metallic materials. Carbon fiber and resin composite materials currently tend to be used to manufacture aircraft structures. The main difference between both materials is that the metallic material is far more conductive than the composite. Therefore, when the effect of an electric discharge is produced in the structure of an aircraft, if it is a metallic structure, the current of this discharge is quickly distributed throughout the entire structure, which does not occur when the structure is made with composite material. This means that the local damage is less with metallic structures than it is in the case of using a composite material.

In the field of aeronautics, to obtain certification for a material it is necessary to conduct tests on the chosen material in certified laboratories for such purpose. These tests are very expensive and complex for the case of composite materials currently used in aeronautics.

The present invention is thus aimed at solving these drawbacks in the case of aircraft structures made of composite material.

SUMMARY OF THE INVENTION

The present invention proposes a method for evaluating the effect of an electric discharge on an aircraft structure made of composite material through the evaluation of the damage caused due to the effect of the thermal heating generated by the mentioned discharge on the structure. The composite material forming the aircraft structure has physical properties and thermal properties that differ according to the chosen direction of the material. This method can approximately estimate these damages and could therefore drastically reduce the number of tests conducted. It will further allow greater freedom when investigating new designs as well as optimize these new designs and those designs already tested.

The method of the invention therefore comprises the steps of:

a) applying an electric discharge on the material of the aircraft structure, modeled as an intensity generator;
b) distributing in an electric mesh with resistive electric elements the material of the aircraft structure;
c) calculating the intensities running through the electric mesh of the material of the aircraft structure from the intensity introduced in the generators;
d) calculating with the previous intensities the heat which is dissipated in each of the elements of the electric mesh of the material of the aircraft structure;
e) calculating the distribution of temperatures in each of the elements of the electric mesh of the material of the aircraft structure;
f) determining the elements of the electric mesh of the material of the aircraft structure which, due to the effect of the distribution of temperatures, experience a change of state and evaporate;
g) determining the damage caused to the material of the aircraft structure due to the effect of the electric discharge.

Other features and advantages of the present invention will be deduced from the following detailed description of an illustrative embodiment of its object in relation to the attached figures.

DETAILED DESCRIPTION OF THE INVENTION

Figure 1:
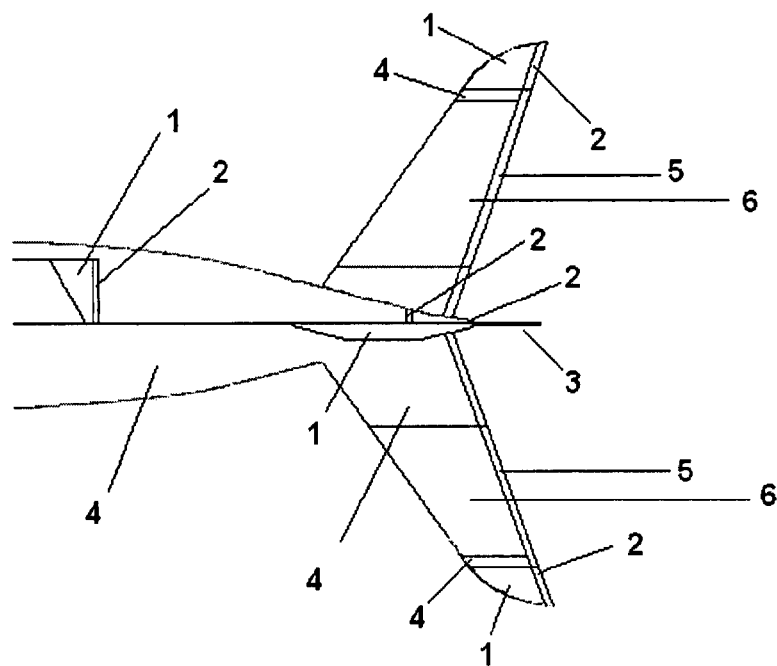
FIG. 1 shows the classification into areas of an aircraft according to the probability thereof of experiencing an impact from an electric discharge.

The present invention therefore provides a method for evaluating the effect of an electric discharge on an aircraft structure made of composite material through the evaluation of the damage due to the effect of thermal heating caused by the mentioned discharge on the structure. The probability of an aircraft suffering a lightening bolt impact is high, it being calculated that an aircraft experiences on average almost 2 lightening bolt impacts per year. Therefore, it is necessary to take the necessary steps assuring firstly the safety of the passengers, and secondly making this lightening bolt impact have the smallest possible effect on the operation of the aircraft.

Not all the parts forming an aircraft structure have the same probability of experiencing the impact of an electric discharge, or that this impact is as severe in all parts. According to the probability and severity of the lightening bolt or the electric discharge, the airplane is split into different areas from the direct impact point of view, the protection of the outer structure of the aircraft thus depending on what region the part to be protected is located in. An aircraft structure is split into the following regions:

Region 1, in which it will probably experience the initial lightening bolt impact and the first return impacts and in which the lightening bolt will probably not remain;

Region 2, in which it will probably experience the initial lightening bolt impact and the first return impacts, and in which the lightening bolt will probably remain;

Region 3, in which there will probably be a return impact with a small amplitude, and furthermore in which the probability that the lightening bolt will remain is low;

Region 4, in which a first impact will probably not be experienced, but in which re-impacts due to the sweeping of the lightening bolt will probably be experienced and in which the lightening bolt will probably not remain;

Region 5, in which a first impact will probably not be experienced, but in which re-impacts due to the sweeping of the lightening bolt will probably be experienced an in which the lightening bolt will probably remain;

Region 6, in which any type of lightening bolt impact will probably not occur, but in which the current associated to the lightening bolt impacts in other areas will have to be conducted.

The method of the invention thus comprises the following steps described in detail below.

1. Applying an Electric Discharge on the Material of the Aircraft Structure by Means of an Intensity Generator The physical phenomenon which is applied on the material of the aircraft structure is that of an electric discharge or lightening bolt. The electric discharge occurs from a focal point which is at a much higher potential than the object on which the discharge falls, which is the object of study. When this potential difference exceeds the dielectric capacity of the medium (in this case, air), an electric arc is formed between the focal point and the object, which allows studying the discharge of a lightening bolt (electric arc) from a cloud (focal point) in the field of aeronautics.

The electric arc is characterized by certain magnitudes, such as the diameter of the arc, which is obtained from the data obtained by means of tests, the intensity that is transferred, the curvature of the arc, the angle of incidence of the lightening bolt, etc. According to the method of the invention, the arc is considered perpendicular to the material of the aircraft structure under study.

Given that in the field of aeronautics the electric discharge is considered to be a function of the current intensity transmitted by this discharge over time, in the method according to the invention the electric discharge is represented by means of a direct current generator, further considering that the current density is constant in the cross section of the electric arc and that the properties of the electric arc do not change over time (stationary electric arc).

Figure 2:
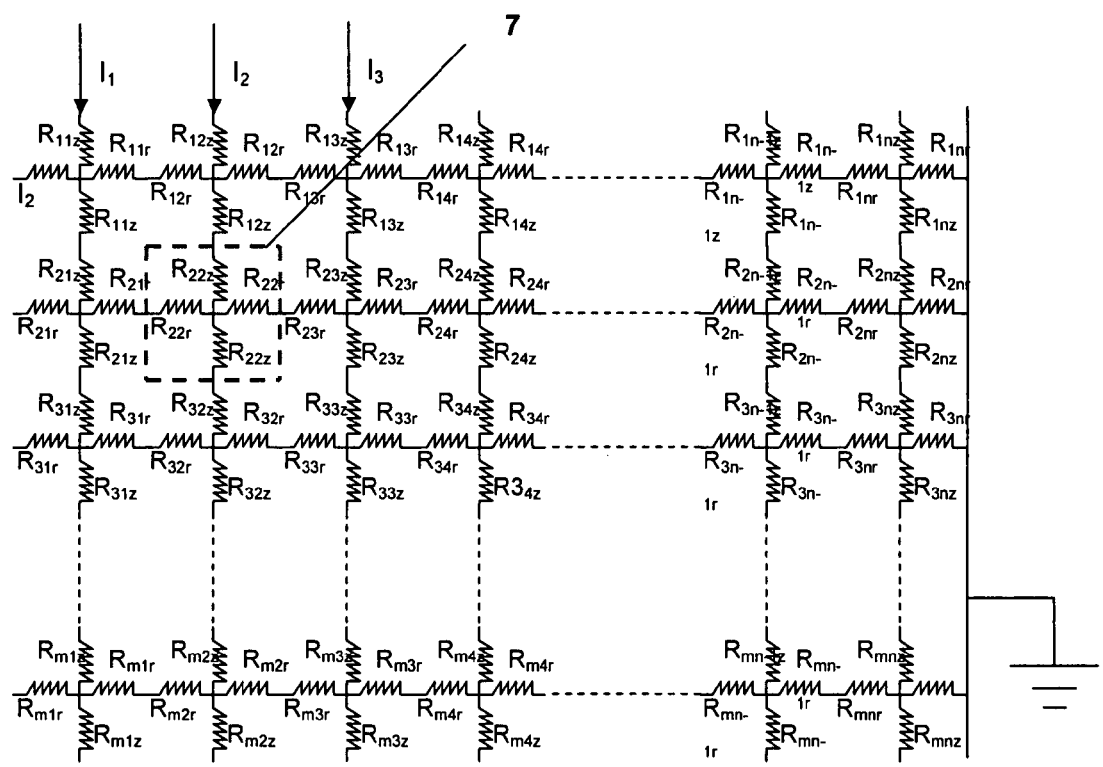
FIG. 2 shows the distribution of the aircraft structure by means of a mesh of resistive electric elements.

2. Distributing in an Electric Mesh with Resistive Electric Elements the Material of the Aircraft Structure According to the method of the invention the material will be split into smaller parts called cells 7. A resistive contact R will be defined between each of these cells 7 and the adjacent cells. The material of the aircraft structure is therefore modeled as a mesh 8 of resistances R, as can be seen in FIG. 2. The ends of this mesh are joined so that all of them are at the same potential, simulating the current return.

The designed method allows including the performance of several classes of material, "z" referring to the direction of the thickness and defining the "xy" plane as the plane locally perpendicular to the "z" axis; the material has a conductivity which may change according to "z", i.e. in each "xy" plane there may be a different electric and thermal conductivity.

The method of the invention thus allows evaluating composite materials (the electric properties of which change in each layer of the stack), as well as homogenous metallic materials. It also allows introducing layers of other different material. For example, a composite material plus a mesh made of a metallic material on the surface of the composite material, a design that is widely used in the field of aeronautics for protecting structures against electric discharges, can be evaluated.

3. Calculating the Intensities Running Through the Electric Mesh of the Material of the Aircraft Structure from the Intensity Introduced in the Generators The electric mesh 8 of the material of the aircraft structure is resolved by a standard electric circuit resolution method from the intensity which is introduced in the mentioned mesh 8 by the direct current generators.

4. Calculating, with the Previous Intensities, the Heat which is Dissipated in Each of the Elements of the Electric Mesh of the Material of the Aircraft Structure From the thermal point of view, the method of the invention considers the material of the aircraft structure as anisotropic, i.e. it considers that its thermal properties depend on the direction.

Since the contour conditions of the material are considered adiabatic, except in the interface between the lightening bolt and the test piece, in which the lightening bolt injects heat into the material, the electromagnetic energy which is introduced in the material is concentrated therein, not taking into account the possible energy that the lightening bolt itself is to radiate.

In the electric mesh described above, the current return is modeled as ground, meaning that the ends of the material are at the same potential, as can be seen in FIG. 2.

5. Calculating the Distribution of Temperatures in Each of the Elements of the Electric Mesh of the Material of the Aircraft Structure In the method being described, there are two thermal energy sources: the interaction in the interface between the electric arc and the material, and the heating of the material due to the Joule effect when the intensity circulates inside it.

This heat generated in the material of the aircraft structure will be diffused by conduction inside the mentioned material.

Figure 3:
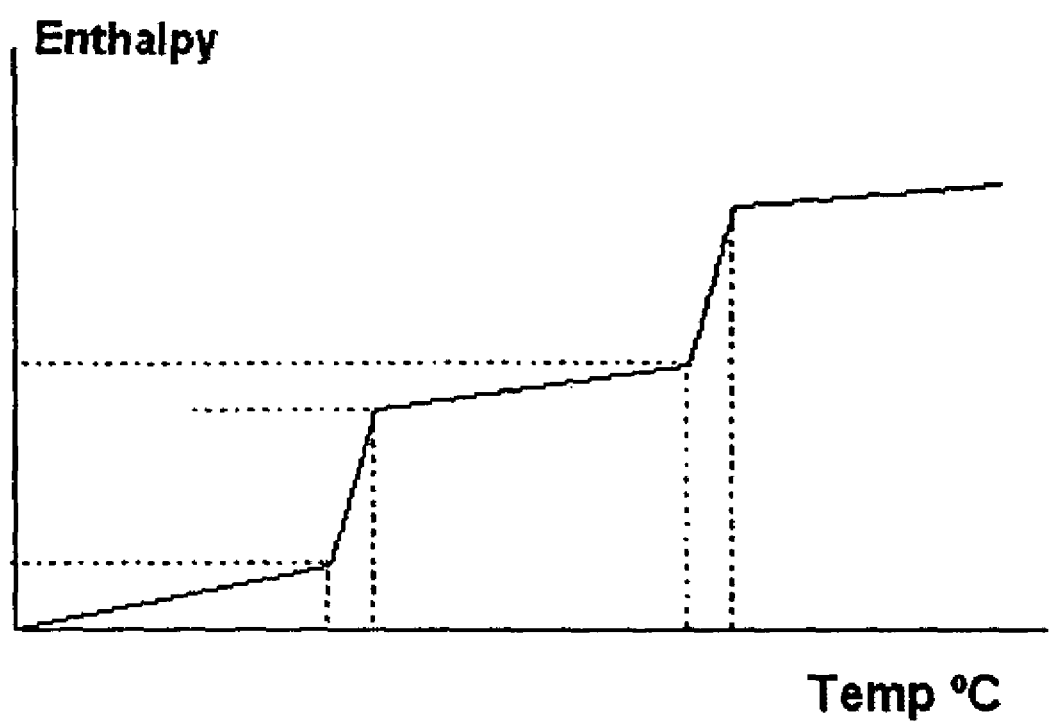
FIG. 3 shows the thermal behavior of the material of the aircraft structure.

6. Determining the Elements of the Electric Mesh of the Material of the Aircraft Structure which, Due to the Effect of the Distribution of Temperatures, Experience a Change of State and Evaporate For severe electric discharges, the energy transferred to the material will be enough to cause a change of state. The change of state is shown in FIG. 3. When it reaches the gaseous state, the cell 7 of the electric mesh 8 of the material of the aircraft structure is no longer taken into account for the purpose of transmitting heat, all the energy that the cell 7 had up to that point from the evaporation being transferred to the cell immediately under it.

7. Determining the Damage Caused to the Material of the Aircraft Structure Due to the Effect of the Electric Discharge After the process has concluded, the cells 7 which have been evaporated are obtained and the damaged caused in the material of the aircraft structure can be evaluated.

Any modifications comprised within the scope defined by the following claims can be introduced in the preferred embodiment described above.

The invention claimed is:

1. A method for evaluating the effect of an electric discharge on an aircraft structure through the evaluation of the damage caused by the effect of the thermal heating generated by the mentioned discharge on the structure, comprising the steps of:
    a) applying an electric discharge on the material of the aircraft structure, modeled as an intensity generator;
    b) distributing in an electric mesh with resistive electric elements, the material of the aircraft structure;
    c) calculating the intensities running through the electric mesh of the material of the aircraft structure from the intensity introduced in the generators;

d) calculating with the calculated intensities running through the electric mesh, the heat which is dissipated in each of the elements of the electric mesh of the material of the aircraft structure;

e) calculating the distribution of temperatures in each of the elements of the electric mesh of the material of the aircraft structure;

f) determining the elements of the electric mesh of the material of the aircraft structure which, due to the effect of the distribution of temperatures, experience a change of state and evaporate;

g) determining the damage caused to the material of the aircraft structure due to the effect of the electric discharge.

2. A method for evaluating the effect of an electric discharge on an aircraft structure according to claim 1, characterized in that the electric discharge is characterized by the diameter of the electric arc, the intensity transferred by the arc, the curvature of the arc and the angle of incidence of the lightening bolt.

3. A method for evaluating the effect of an electric discharge on an aircraft structure according to claim 2, characterized in that the electric arc is perpendicular to the material of the aircraft structure.

4. A method for evaluating the effect of an electric discharge on an aircraft structure according to claim 1, characterized in that the electric discharge is represented by means of a direct current generator, the current density being constant in the cross section of the electric arc and the properties of the electric arc not changing over time.

5. A method for evaluating the effect of an electric discharge on an aircraft structure according to claim 1, characterized in that the material of the aircraft structure is modeled as a mesh (8) comprising cells (7), said cells (7) in turn comprising a resistance (R) between each of the cells (7) and the adjacent cells, the ends of the mesh (8) being joined so that all of them are at the same potential.

6. A method for evaluating the effect of an electric discharge on an aircraft structure according to claim 5, characterized in that the current return in the electric mesh (8) is modeled as ground, the ends of the material thus being at the same potential.

7. A method for evaluating the effect of an electric discharge on an aircraft structure according claim 1, characterized in that the contour conditions of the material are adiabatic.

8. A method for evaluating the effect of an electric discharge on an aircraft structure according to claim 1, characterized in that the aircraft structure is made of a composite material.

9. A method for evaluating the effect of an electric discharge on an aircraft structure according to claim 1, characterized in that the aircraft structure is made of a homogenous metallic material.

10. A method for evaluating the effect of an electric discharge on an aircraft structure according to claim 1, characterized in that the aircraft structure is made of a composite material with a metallic material mesh on the surface thereof.

* * * * *